United States Patent
Keusch et al.

(10) Patent No.: US 6,377,847 B1
(45) Date of Patent: Apr. 23, 2002

(54) IONTOPHORETIC DRUG DELIVERY DEVICE AND RESERVOIR AND METHOD OF MAKING SAME

(75) Inventors: Preston Keusch, Hazlet, NJ (US); NRK Vilambi, Jamaica Estates, NY (US); Bruce Michael Eliash, Franklin Lakes, NJ (US)

(73) Assignee: Vyteris, Inc., Fair Lawn, NJ (US)

(*) Notice: Subject to any disclaimer, the term of this patent is extended or adjusted under 35 U.S.C. 154(b) by 0 days.

(21) Appl. No.: 09/328,329

(22) Filed: Jun. 9, 1999

Related U.S. Application Data

(63) Continuation-in-part of application No. 08/533,979, filed on Sep. 26, 1995, now abandoned, which is a continuation-in-part of application No. 08/129,222, filed on Sep. 30, 1993, now abandoned.

(51) Int. Cl.[7] ................................................. A61N 1/30
(52) U.S. Cl. ........................................ 604/20; 607/149
(58) Field of Search .................... 604/20, 501; 607/149

(56) References Cited

U.S. PATENT DOCUMENTS

| | | | |
|---|---|---|---|
| 4,706,680 A | * | 11/1987 | Keusch et al. |
| 4,989,607 A | * | 2/1991 | Keusch et al. |
| 5,143,071 A | * | 9/1992 | Keusch et al. |
| 5,312,326 A | * | 5/1994 | Myers et al. |
| 5,320,598 A | * | 6/1994 | Haak et al. |
| 5,328,455 A | * | 7/1994 | Lloyd et al. |
| 5,374,241 A | * | 12/1994 | Lloyd et al. |
| 6,032,073 A | * | 2/2000 | Effenhauser |

* cited by examiner

*Primary Examiner*—Mark Bockelman
(74) *Attorney, Agent, or Firm*—Kirkpatrick & Lockhart LLP

(57) ABSTRACT

A reservoir electrode assembly of the present invention for an iontophoretic drug delivery device includes an electrode and a hydrophilic reservoir situated in electrically conductive relation to the electrode. The hydrophilic reservoir is formed from a bibulous hydrophilic cross-linked polymeric material having a first surface and a second surface that is adhesively adherent to the electrode. The first surface of the polymeric material is releasably adhesively adherent when applied to an area of a patient's skin. The polymeric material has a cohesive strength forms an adhesive bond with a bond strength between the second surface of the polymeric material to the electrode that is greater than the cohesive strength of the polymeric material. Additionally, an adhesive bond strength of the first surface of the polymeric material to the applied area of the patient is less than the cohesive strength of the polymeric material so that upon removal of the reservoir assembly of the invention from the applied area of the patient, substantially no polymeric material remains on the applied area and the hydrophilic reservoir remains substantially intact and adhesively adherent to the electrode.

20 Claims, 8 Drawing Sheets

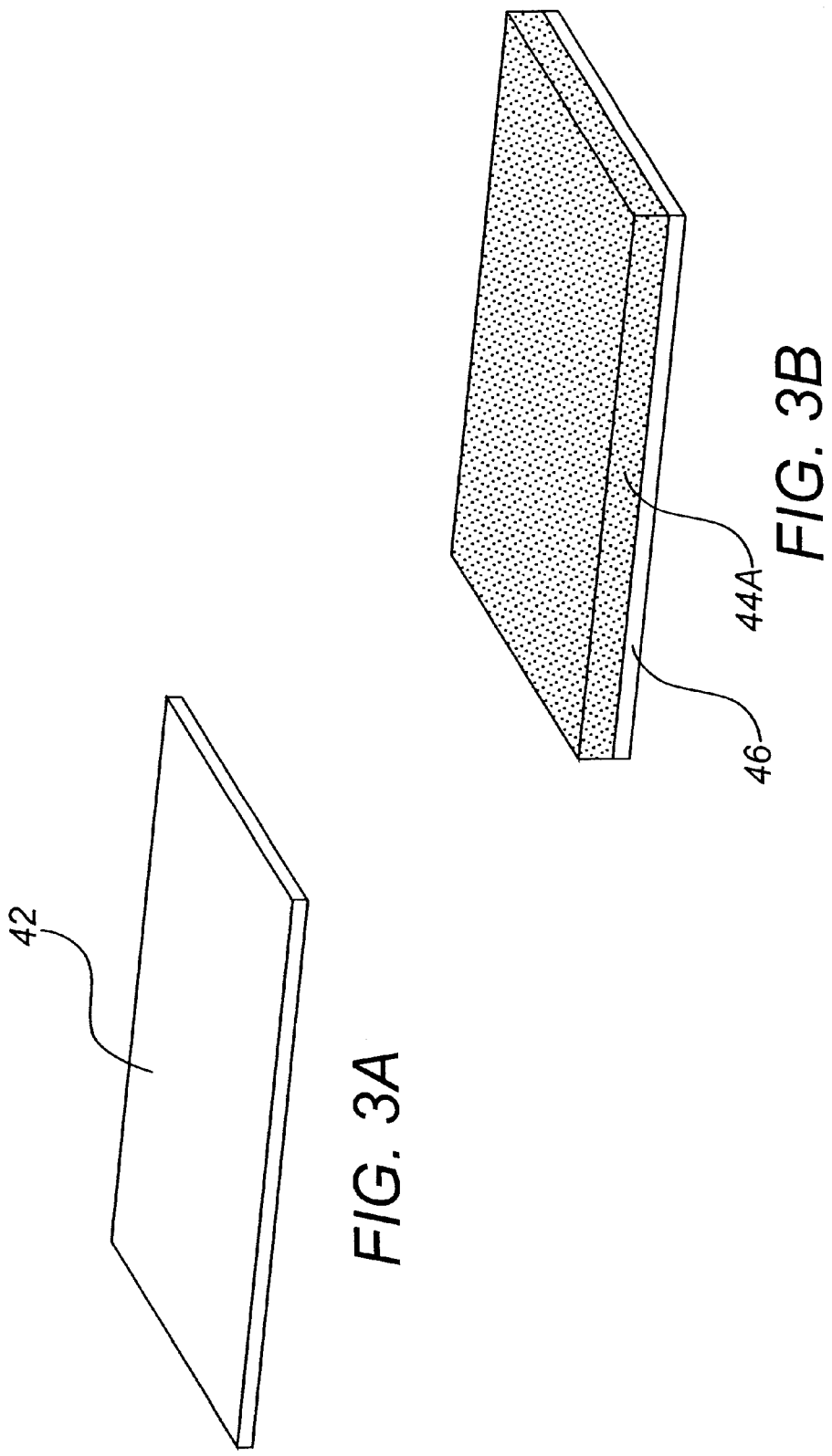

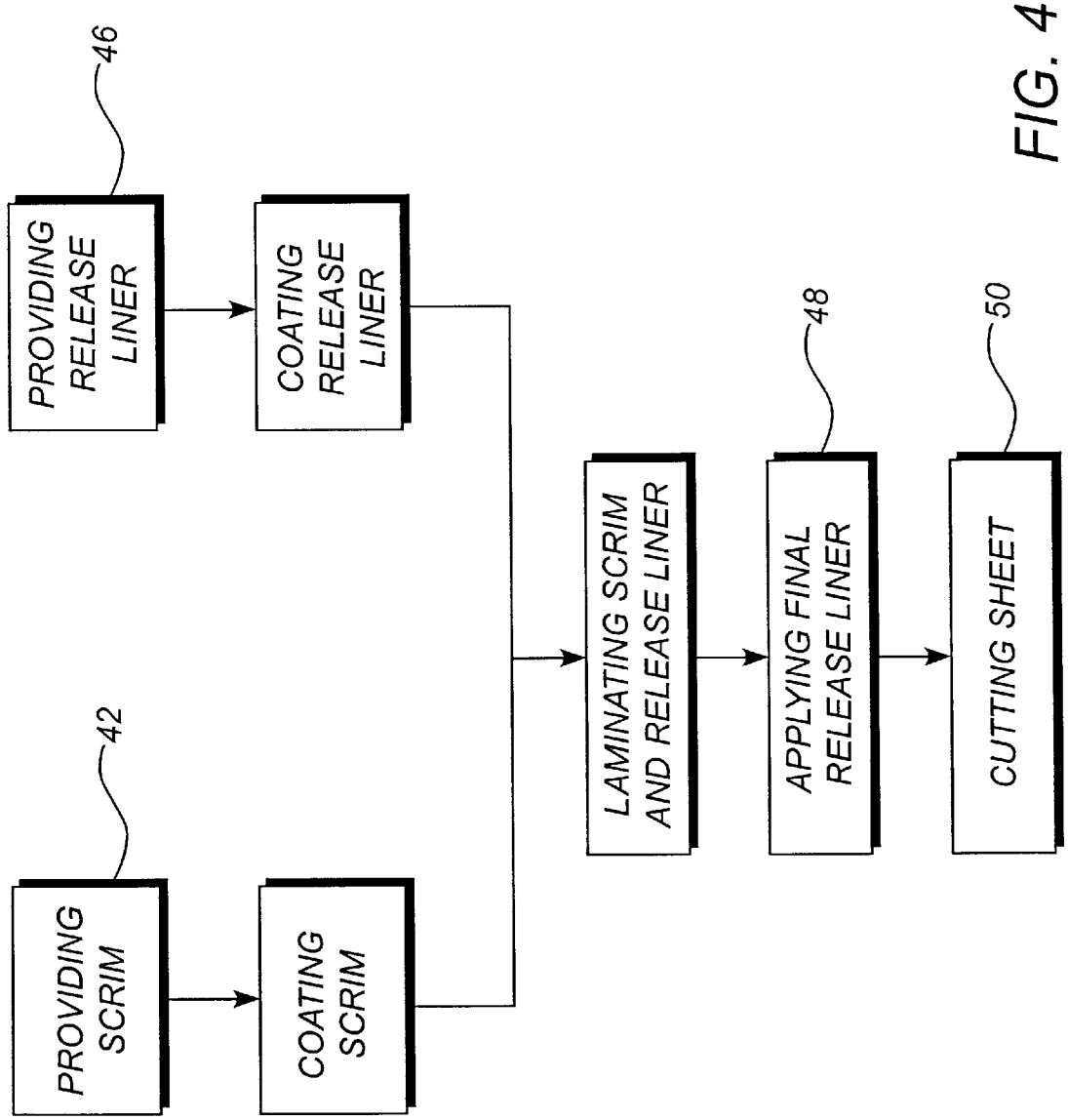

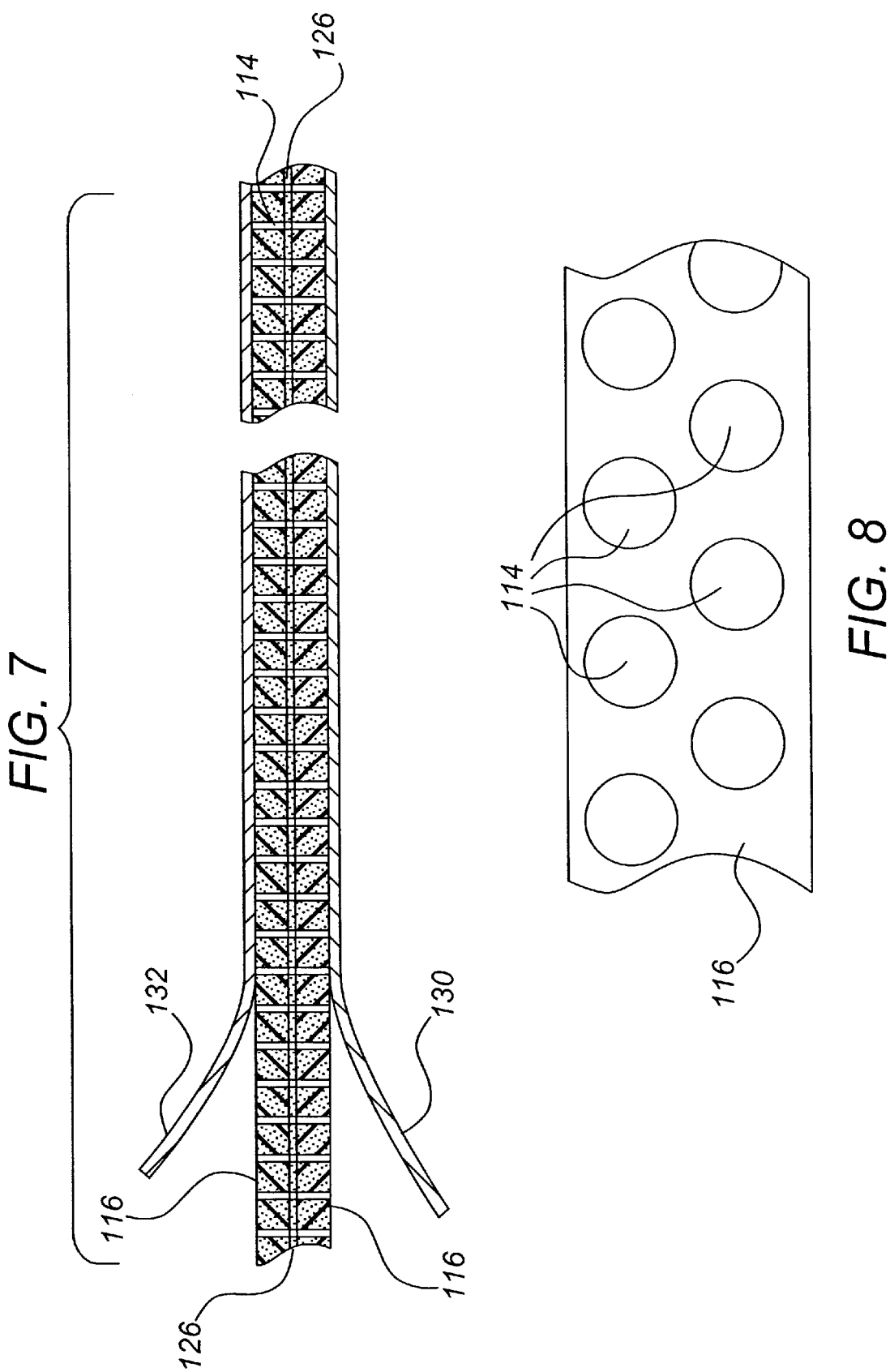

IONTOPHORETIC DRUG DELIVERY DEVICE AND RESERVOIR AND METHOD OF MAKING SAME

This application is a continuation-in-part of application Ser. No. 08/533,979 filed Sep. 26, 1995, now abandoned which is a continuation-in-part of application Ser. No. 08/129,222 filed Sep. 30, 1993, now abandoned.

FIELD OF THE INVENTION

The present invention generally relates to iontophoretic systems for delivering medicaments such as therapeutic drugs and medicines to patients transdermally, i.e., through the skin, and more specifically relates to a stable iontophoretic drug delivery device and a reservoir for use in the same. In addition, the present invention relates to a method for making a stable iontophoretic drug delivery device with long shelf life and the reservoir for use in such a device.

BACKGROUND

Transdermal drug delivery systems have, in recent years, become an increasingly important means of administering drugs. Such systems offer advantages clearly not achievable by other modes of administration such as avoiding introduction of the drug through the gastro-intestinal tract or punctures in the skin to name a few.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user, such as a patient, using iontophoresis, which according to Stedman's Medical Dictionary, is defined as "the introduction into the tissues, by means of an electric current, of the ions of a chosen medicament."

Conventional iontophoretic devices, such as those described in U.S. Pat. Nos. 4,820,263 (Spevak et al.), U.S. Pat. No. 4,927,408 (Haak et al.) and U.S. Pat. No. 5,084,008 (Phipps), the disclosures of which are hereby incorporated by reference, for delivering a drug or medicine transdermally through iontophoresis, basically consist of two electrodes—an anode and a cathode. Usually, electric current is driven from an external supply into the skin at the anode, and back out at the cathode. Accordingly, there has been considerable interest in iontophoresis to perform delivery of drugs for a variety of purposes. Two such examples, involve the use of Novocaine,™ which is usually injected prior to dental work to relieve pain, and Lidocaine, which is usually applied as a topical, local anesthetic.

Such prior devices have prior hereto not been pre-loaded and self adhering, e.g., they have typically utilized an absorbent pad or porous solid sheet that can be filled with drug solution as the drug reservoir. These absorbent pads or porous sheets have three major disadvantages. First, they must be filled with the drug solution after removal from the package since these pads or porous sheets do not hold the drug solution as the solution is subject to removal and leakage under pressure or flexure. In addition, even after the inconvenient addition of the drug solution and after removal from the package, the absorbent pad or porous sheet reservoir remain subject to leakage and smearing of the drug solution due to pressure or flexure upon the skin. Furthermore, absorbent pads or porous solid sheets can not provide the electrical continuity to complete intimate contact since they lack adhesiveness and flexibility with the skin and its contours.

In addition, prior drug reservoirs have included pastes and unformed viscous semi-solid gels such as for example agar that have both solid and liquid characteristics as described, for example, in U.S. Pat. No. 4,383,529 (Webster), the disclosure of which is hereby incorporated by reference.

Powers et al., U.S. Pat. No. 4,886,277, although suggesting that Lidocaine could be incorporated into the reservoir, fails to solve the resulting problem associated with compatibility with adjacent materials such as conductive layers. Accordingly, such a device would fail to provide sufficient stability for extended shelf life, i.e., more than one year.

However, several disadvantages and limitations have been associated with the use of such devices, including handleability and loadability. For example, the semi-solid agar reservoir disclosed in Webster flows under shear or stress. Furthermore, this disclosed reservoir may melt upon exposure to modest elevated temperatures. The agar is unstable, spontaneously releasing aqueous solution.

Thus, there has been a need for an iontophoretic drug delivery device and a reservoir for use in the same, as well as a method for making the reservoir, which would eliminate the problems and limitations associated with the prior devices discussed above, most significant of the problems being associated with stability, handleability, loadability and electrocontinuity of the reservoir, including chemical and thermal stability of the reservoir and the electrode.

SUMMARY

A reservoir electrode assembly of the present invention for an iontophoretic drug delivery device includes an electrode and a hydrophilic reservoir situated in electrically conductive relation to the electrode. The hydrophilic reservoir is formed from a bibulous hydrophilic cross-linked polymeric material having a first surface and a second surface that is adhesively adherent to the electrode. The first surface of the polymeric material is releasably adhesively adherent when applied to an area of a patient's skin. The polymeric material has a cohesive strength forms an adhesive bond with a bond strength between the second surface of the polymeric material to the electrode that is greater than the cohesive strength of the polymeric material. Additionally, an adhesive bond strength of the first surface of the polymeric material to the applied area of the patient is less than the cohesive strength of the polymeric material so that upon removal of the reservoir assembly of the invention from the applied area of the patient, substantially no polymeric material remains on the applied area and the hydrophilic reservoir remains substantially intact and adhesively adherent to the electrode.

The reservoir electrode of the present invention provides solutions for several problems seen with available iontophoretic reservoir electrodes. The reservoir electrode of the invention, by being adherent to the skin of the patient minimizes current pathway concentrations that often result in irritation and burning caused by incomplete contact of the reservoir electrode assembly to the patient's skin. Because the adhesive bond of the electrode to the patient's skin is less than the cohesive strength of the polymeric material used for the reservoir, substantially no residue from the reservoir material is left behind on the patient's skin. Additionally, since the polymeric reservoir material forms an adhesive bond with the electrode, there is intimate and effective electrical contact between the electrical circuit and the polymeric reservoir material. The reservoir electrode assembly of the invention can be physically smaller than most currently available electrode assemblies because the entire polymeric reservoir is hydrophilic and is utilized to contain drugs and electrolytes. Many current electrode assemblies require hydrophobic polymeric materials to achieve an adhesive tack and another hydrophilic material to retain the aqueous drug and electrolyte used for the iontophoretic delivery. When a hydrophobic and a hydrophilic component are used to form a reservoir, as in the currently available materials, some partitioning of the medicament may occur or there may be some binding of the active compound with the hydrophobic material that reduces the availability of the medicament for delivery. These effects are not seen with the hydrophilic reservoir of the invention.

In contrast to the prior devices discussed above, it has been found that a iontophoretic drug delivery device particularly suited for use to deliver at least one medicament, particularly in a high dose efficiency, can be constructed in accordance with the present invention by the incorporation of an aqueous swollen cross linked water soluble polymeric drug delivery reservoir adhesively coupled to the electrode such that the adhesive strength of the electrode material is greater than the cohesive strength of the reservoir material. In addition, the device of the present invention can easily fit over any contour of the body and provide excellent electrocoupling with the electrode and the skin, while still being capable of flexing and adhering to the skin. Also the device of the present invention can be applied over a range of temperatures and is stable for over one year at controlled room temperature to provide a commercially advantageous shelf-life.

The iontophoretic drug delivery device of the present invention for delivering at least one medicament to an applied area of a patient, such as the skin, mucous membrane and the like, including electrode assembly means for driving a medication into the applied area of the patient to be absorbed by the body of the patient, the electrode include an electrode material, and a covalently cross linked hydrophilic reservoir situated in electrically conductive relation to the electrode assembly means, with the reservoir including an aqueous swollen cross linked water soluble polymer material having an adhesive strength to the electrode material, an adhesive strength to the applied area and a cohesive strength to itself, with the reservoir containing at least one medicament, wherein the adhesive strength of the polymer material to the electrode material is greater than the cohesive strength of the polymer material and the adhesive strength of the polymer material to the applied area is less than the cohesive strength of the polymer material so that upon removal of the device from the applied area little if any polymer material remains on the applied area, while maintaining the reservoir intact and in intimate contact with the electrode material.

In the preferred embodiment, the device of the invention further includes a structurally reinforcing member situated within the reservoir including the aqueous swollen cross linked water soluble polymer, with the structurally reinforcing member having an open area that is thin and of sufficient voidage so as not to impede the flow of ions. In addition, the structurally reinforcing member is a thermoplastic polymeric scrim and the aqueous swollen cross linked water soluble polymer is cross linkable by high energy irradiation with the scrim being wettable enough and with open area of greater than 40% to insure phase continuity though the scrim, along with sufficient adhesion to contribute strength to the aqueous cross linked polymeric reservoir. Also, the aqueous swollen cross linked water soluble polymer is selected from the group including polyethylene oxide, polyvinyl pyrrolidone, polyvinyl alcohol, polyethylene glycol, and polyacrylamide. The at least one medicament includes Lidocaine and the reservoir also includes a vasoconstrictor, stabilizers and glycerin. Further, the reservoir further includes additives and conductive salts, with the additives selected from the group including glycerin, propylene glycol, polyethylene glycol and preservatives.

The reservoir of the present invention for use in an iontophoretic drug delivery device having an electrode assembly including an electrically conductive electrode material for delivering at least one medicament through an applied area of a patient, such as the skin, mucous membrane and the like, includes a layer of a aqueous swollen cross linked water soluble polymer material capable of having electrocontinuity with the electrode assembly, with the aqueous swollen cross linked water soluble polymer material having sufficient adhesive tack including the at least one medicament for delivery through an applied area of a patient, such as the skin, mucous membrane and the like, and the aqueous swollen cross linked water soluble polymer material having an adhesive strength to the electrode material greater than the cohesive strength of the polymer material, and the cohesive strength being greater than an adhesive strength to the applied area.

In the preferred embodiment, the reservoir also includes a structurally reinforcing member situated within the layer of aqueous swollen cross linked water soluble polymer material, with the structurally reinforcing member having approximately 40% porosity so as not to impede the flow of ions, with the structurally reinforcing member being a wettable, scrim of a aqueous insoluble thermoplastic polymeric material and the aqueous swollen cross linked water soluble polymer material is cross linked by high energy irradiation. Also, aqueous swollen cross linked water soluble polymer is selected from the group including polyethylene oxide, polyvinyl pyrrolidone, polyvinyl alcohol, polyacrylamide and polyethylene glycol. In addition, the at least one medicament includes Lidocaine and the aqueous swollen cross linked water soluble polymer material includes a vasoconstrictor, stabilizers and glycerin. Further, the reservoir includes additives and conductive salts, with the additives selected from the group including glycerin, propylene glycol and polyethylene glycol and preservatives.

The method of making a reservoir for an iontophoretic drug delivery device of the present invention includes the steps of providing a structurally reinforcing member, coating the reinforcing member with a viscous water soluble polymer solution on both sides of the structurally reinforcing member such that the polymer solution penetrates the open area, wets the reinforcing member, and cross linking the layer by high energy irradiation, with the cross-linked layer of polymer having an adhesive strength to an electrode material greater than a cohesive strength of the polymer, and the cohesive strength being greater than an adhesive strength to an applied area.

In the preferred embodiment of the method, the step of coating includes the steps of applying a layer of the viscous solution to one side of the reinforcing member, applying a layer of the viscous solution to one side of a release liner and laminating the release liner and the reinforcing material together such that both surfaces of the reinforcing member are coated with the viscous solution. In addition, the viscous solution is applied to the reinforcing member and the release liner to a thickness of about Ca. 5 mil to 70 mil. The method also includes the step of applying final release liners to the remaining exposed viscous solution coated surfaces of the reinforcing member to form a laminate and cross linking the viscous solution. Also, the method includes the steps of replacing one of the final release liners with an electrode in flexible sheet form, and adding at least one medicament to the cross linked water soluble polymer, with the at least one medicament includes Lidocaine and the cross linked water soluble polymer includes a vasoconstrictor, stabilizers, glycerin and preservative. Further, the method includes the of cutting the laminate into a suitable shape and area and laminating it to a conductive metal for use in an iontophoretic drug delivery device.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

FIGS. 3A, 3B, 3C and 3D are schematic views of the various steps of the method for making the reservoir of the present invention;

FIG. 4 is a logic flow diagram depicting the various steps of the method for making the reservoir of the present invention;

FIG. 7 is a schematic cross-sectional view of the coating and cross-linking of the web for forming the PVP reservoir; and FIG. 8 is a schematic top plan view of the web illustrating punching out individual reservoir units.

DETAILED DESCRIPTION

Figure 1:
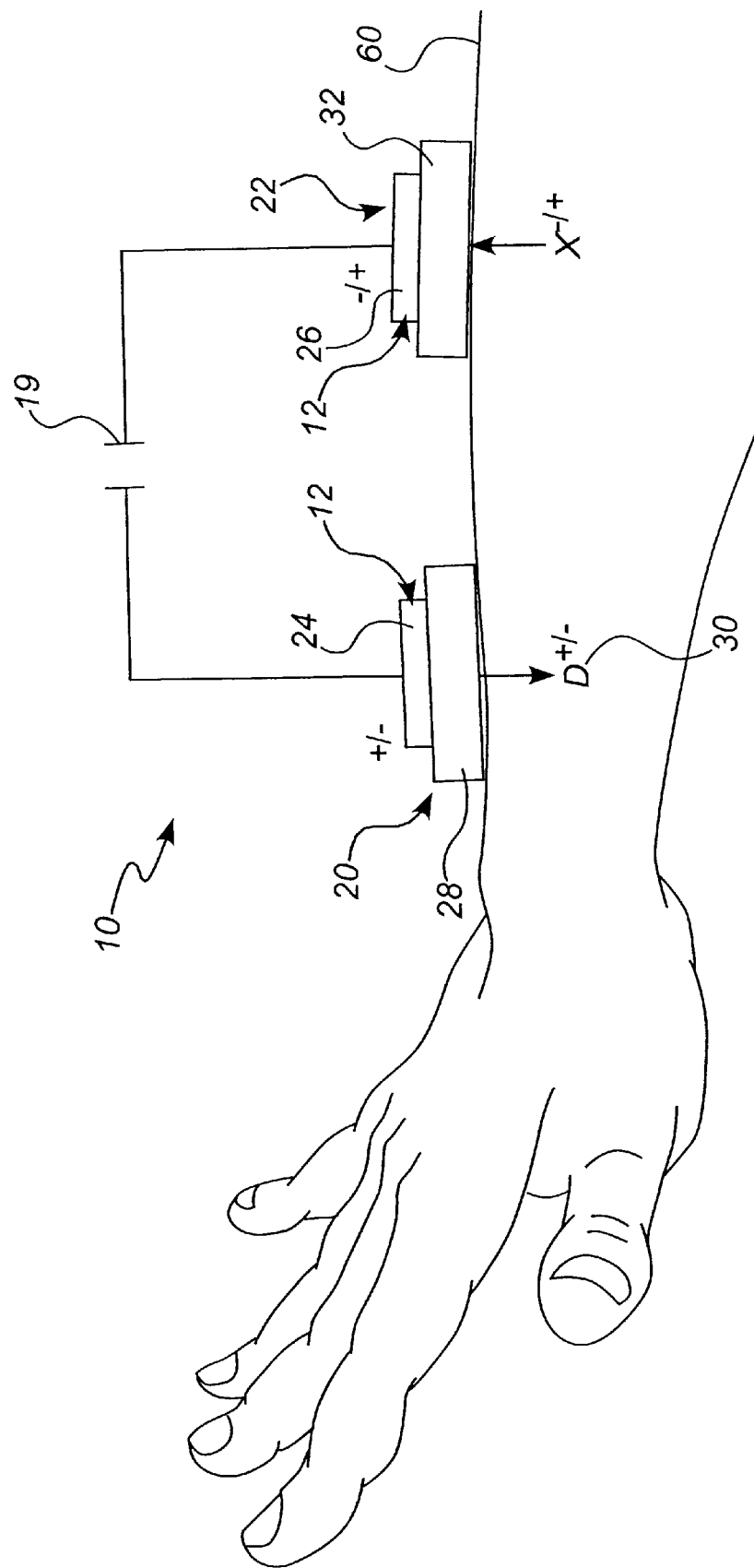
FIG. 1 is a schematic view of the iontophoretic drug delivery device of the present invention illustrating placement of the device on a user.
Figure 2:
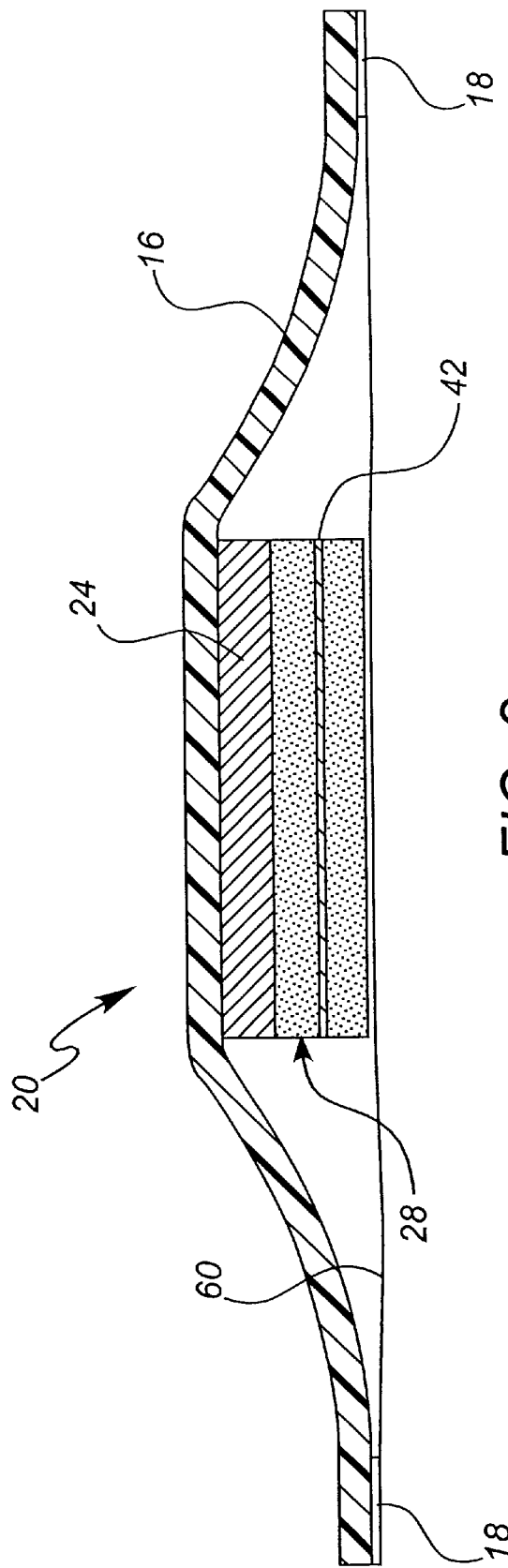
FIG. 2 is a cross sectional view of the device of the present invention.

The iontophoretic drug delivery device of the present invention is illustrated in FIGS. 1 and 2, and generally includes the designation 10. Referring to FIGS. 1 and 2, the device 10 of the present invention includes an electrode assembly 12, having at least one electrode and at least one reservoir, with the reservoir and electrode held or contained within a suitable structure 16, with a skin adhesive 18. Also, as is well known in the art, a power source 19 is provided in circuit with the electrode assembly 12 for supplying a source of electrical current. It should be appreciated that a return electrode and reservoir may be combined into a single electrode assembly 12 or separately provided as illustrated in FIG. 1.

In the preferred embodiment, the device is divided or otherwise separated into two portions 20 and 22, with the electrode assembly 12 including two electrodes 24 and 26. One portion 20 (first) includes the electrode 24 and a reservoir 28, with the reservoir being situated adjacent and coupled to the electrode 24 and holding at least one medicament or drug 30, preferably in ionized or ionizable forms, to be delivered iontophoretically. The other portion 22 (second) includes the electrode 26 and a reservoir 32, with the reservoir being situated adjacent to the electrode 26 and holding an electrolyte 34. The particular electrolyte is not essential to the present invention and is merely a matter of choice. However, in this embodiment the electrolyte may include sodium chloride in an aqueous solution, matrix or the like as explained in greater detail hereinbelow.

A schematic diagram of the first portion 20 of the device 10 is illustrated in FIG. 2. In this case, the medicament 30 to be delivered through the skin is a cation and the reservoir 28 is connected to the electrode 24, which acts as an anode. The return electrode 26 (cathode) may be constructed in the manner as the working electrode 24. If the drug is an anion, then the drug containing reservoir would be connected to the cathode and the return reservoir would be connected to the anode.

As is well known within the field, the device can be situated on the area of the patient to which the medicament is to be applied (the applied area) and a voltage impressed across the electrodes 24, 26 of the electrode assembly 12 to cause current to flow through the skin 60 of the patient to drive the ionic medicament locally into the skin and the tissue or to be absorbed systematically by the body of the patient. It should also be appreciated that the device of the present invention can be applied to other areas of the body such as mucous membranes and the like depending upon the desired therapy and medicaments to be delivered.

In order to transport the medicament through intact skin 60 at least the reservoir 28 containing the medicament includes an aqueous swollen cross linked water soluble polymer, which for simplicity is hereinafter referred to as a cross linked water soluble polymer. The cross linked water soluble polymer can be incorporated into the reservoir as a homogeneous solid cut or molded sheet 40 of suitable shape and area which can be attached to the electrode as illustrated in FIGS. 1 and 2. However, it should be appreciated that the reservoir 32 (cathode) may also be made of the same material as the reservoir 28 containing the medicament, i.e., to include the cross linked water soluble polymer sheet 40 illustrated in FIGS. 3A–3D. Accordingly, the cross linked water soluble polymer sheet 40 containing either the medicament and/or the electrolyte serves as the reservoirs 28, 32 and the electrical coupling to the skin while being able to conform to all contours of the body. In addition, the reservoir may include additives selected from the group including glycerin, propylene glycol, polyethylene glycol and conductive salts, as well as preservatives.

The particular cross linked water soluble polymer material may be made from a variety of commercially available water soluble polymers known to those skilled in the art as long as it is of low bioburden, is electrically conductive, readily conforms to the contours of the body, is capable of being cross linked and can hold or otherwise retain the drug solution under pressure and flexure.

Cross linked water soluble polymers are preferred reservoirs as they provide a conformable interface with good electrical coupling and excellent biocompatibility. Examples of such cross linked water soluble polymers are irradiated cross linked polyethylene oxide (PEO), polyvinyl pyrrolidone (PVP), polyvinyl alcohol (PVA), polyethylene glycol (PEG), polyacrylamide and polyethylene glycol (PEG). The cross linked water soluble polymer sheet 40 by nature of its preparation by irradiation cross linking is of low bioburden and is non toxic, non irritating and non sensitizing to the skin. This is particularly assured by the fact that no chemical cross linking agents or organic solvents are required to synthesize the cross linked water soluble polymer material. It should be appreciated, that the techniques of irradiation cross linking the water soluble polymer material are well known in the art.

In the preferred embodiment, the cross linked water soluble polymer sheet 40 may include a netting or non-woven material 42 such as an inert and wettable polyethylene terephthalate (PET) material is the form of a scrim commercially available from Reemay, Inc. The scrim utilized for this application is preferably an open web, inert, water insoluble material that does not change the conductivity or ionic flow of the materials in the water soluble polymer. In addition, the scrim is wettable and porous. The basis weight of the scrim being of a basis weight between Ca. 4 to 60 grams/square yard. Also, in this way, the cross linked water soluble polymer sheet 40 can be formed from a solution 44 of pre-mixes after dispersion and full solution, with the solution then applied on both sides of the scrim 42 to a thickness of Ca. 5 mil to 40 mil and then cross linked by high energy irradiation such as for example, electron beam or gamma irradiation to form covalent cross links. The particular thickness of the cross linked water soluble polymer sheet may vary depending upon, e.g., the medicament to be delivered, the applied area and the like, from a very thin sheet, i.e., film, for high drug efficiency to a very thick sheet for minimization of sensation when an electrical current is applied. However it should also be appreciated that suitable scrim materials may include inorganic materials such as ceramics and composites such as fiber glass.

Figure 3C:
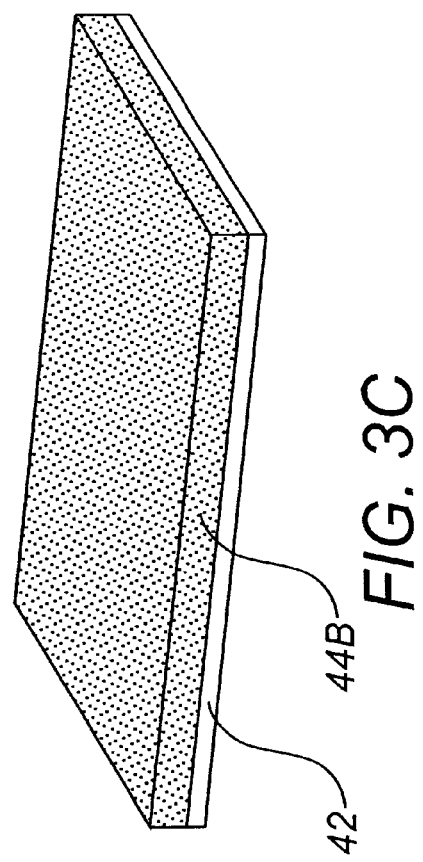
Figure 3D:
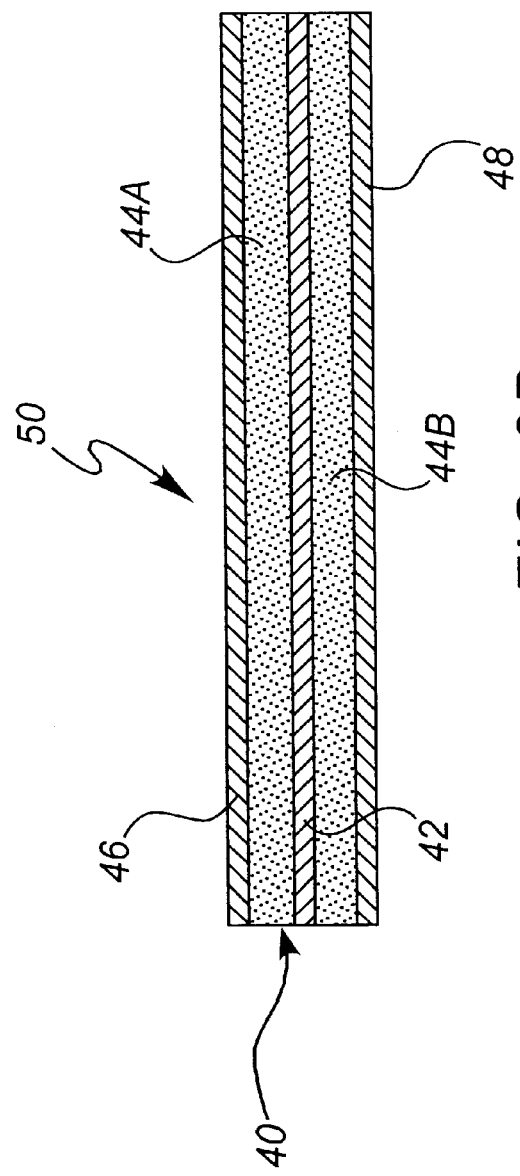
Figure 5:
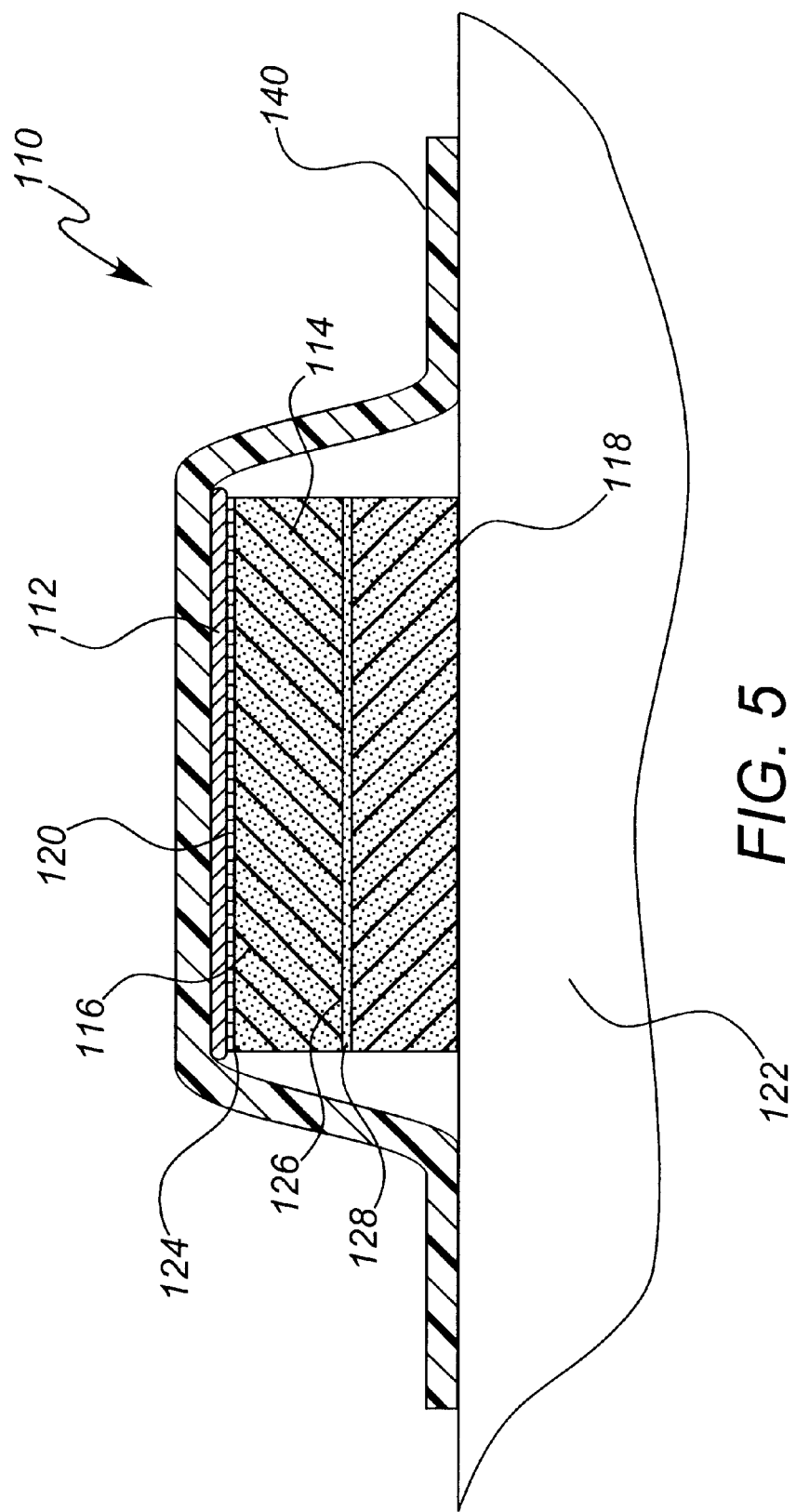
FIG. 5 is a cross-sectional view of the reservoir electrode assembly of the invention.
Figure 6:
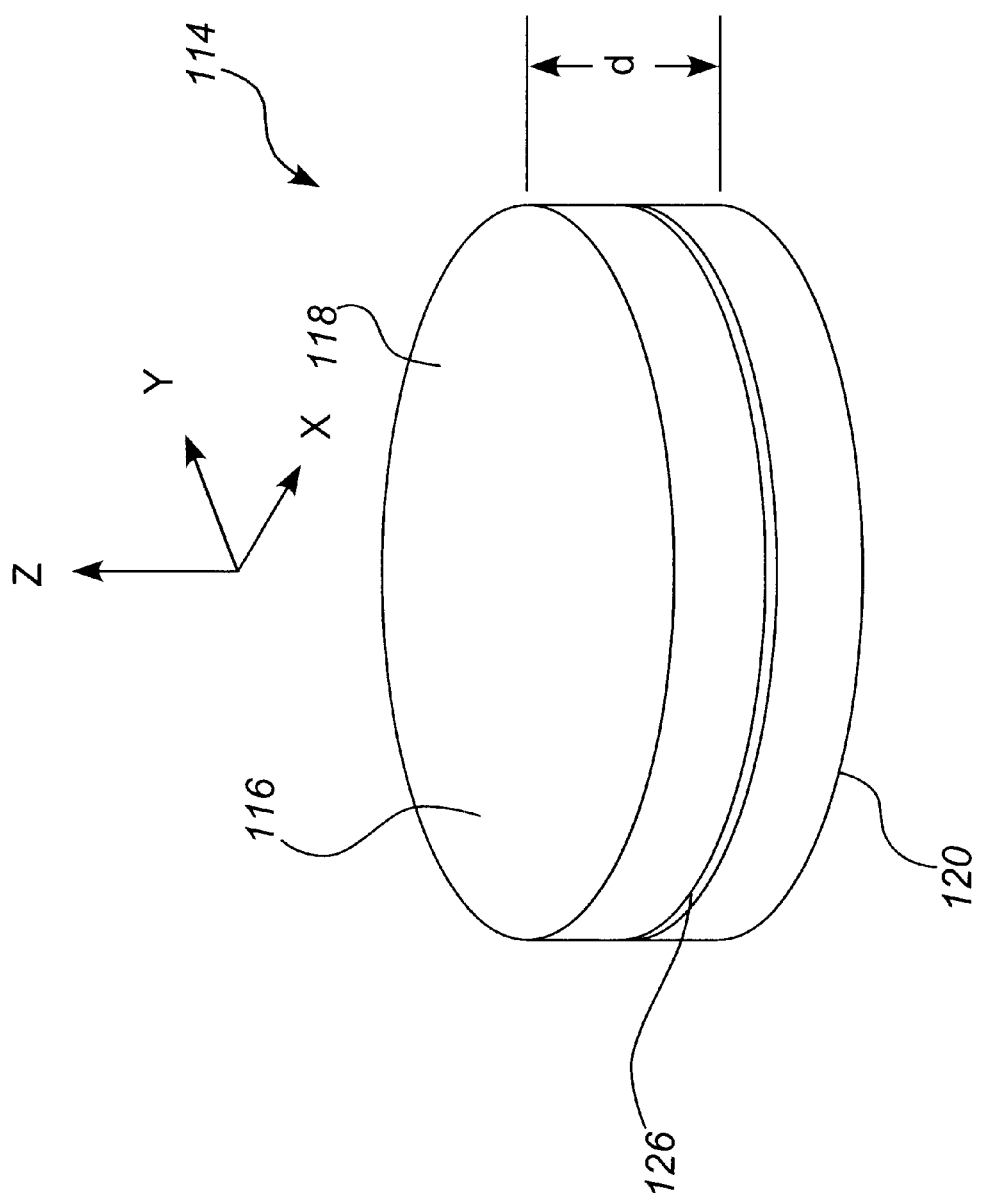
FIG. 6 is a schematic perspective view of the reservoir of the invention from FIG. 5.

As illustrated in FIGS. 3A, 3B, 3C and 3D, and the flow diagram illustrated in FIG. 4, preferably the cross linked water soluble polymer sheet 40 is formed by providing the release liner 46 and the scrim 42, applying or otherwise coating a release liner or other backing material 46 with one-half of the viscous solution 44 of water soluble polymer to form a layer 44A (FIG. 3B) and coating or otherwise applying the other half of the viscous solution 44 to one side of the scrim 42 to form a layer 44B (FIG. 3C). The coated liner 46 is then laminated to the coated scrim 42 such that the scrim has the viscous solution on both sides (FIG. 3D). Next, a final liner or other backing material 48 is then applied to the exposed surface, with the cross linked water soluble polymer sheet 40 sandwiched between the two release liners 46, 48 to form a laminate 50, which in the preferred embodiment is then exposed to high energy irradiation to cross link the water soluble polymer solution. In the alternative, to provide ease of handling, the final release liner 48 can be applied to the coated scrim prior to lamination with the coated liner 46.

The scrim 42 itself imparts structural support and mechanical strength to the final cross linked water soluble polymer sheet to prevent shearing. Thereafter, the laminate 50 can be easily handled and cut or otherwise formed into the desired shape for the particular reservoir 28, 32. In this way, the release liner 46 can be subsequently removed and the exposed surface of the cross linked water soluble polymer adhered to the electrode 24, 26, or removed and the medicament 30 added and the release liner replaced or adhered to the electrode. Also, the release liner 48 can remain until being removed for application of the device 10 to the applied area of the patient.

In the alternative, the release liner 48 (or 46) can be replaced by the electrode in the form of a thin metal sheet or polymer sheet coated with a conductive ink or metal foil laminated to the polymeric sheet such as for example as disclosed in co-pending application Ser. No. 08/012,168 now abandoned, the disclosure of which is hereby incorporated by reference. In this way, the reservoir can be coupled to the electrode in one step. It should also be appreciated that a conductive scrim may be incorporated into the reservoir with the scrim being placed asymmetrically within the reservoir by placing different thicknesses of the viscous solution on each side of the scrim.

The use of an easily handled cross linked water soluble polymer sheet as the reservoir 28, 32 to replace a paste, semi-solid gel or an absorbent pad has many advantages over existing coupling reservoirs. The cross linked water soluble polymer is solid and shape retaining and it exhibits no leakage of medicament or electrolyte under flexure or applied pressure. It is also drapeable and flexible and adhesive to the skin. This assures that the cross linked water soluble polymer maintains the required medicament and electrolyte concentration as well as reproducible delivery by its adherence and conformability to the contours of the skin or other applied area.

Also, the adhesive strength of the gel and the electrode material is greater than the cohesive strength of the gel material and the cohesive strength of the gel is greater than the adhesive strength of the gel to the applied area, e.g., skin of the patient. In this way, a intimate electrical contact between the electrode and the reservoir is achieved which insures electrical continuity (and uniformity) between the interface of the electrode and the gel during applications of he device to the applied area. Also, upon removal of the device, little, if any, material remains on the applied area after removal of the device.

Due to its high water content, the cross linked water soluble polymer is highly conductive to ionic transport, yet in combination with the scrim, it possesses sufficient mechanical strength for processing and use. Also, despite its high water content, the cross linked water soluble polymer is a single phase solid solution which does not synerese liquid spontaneously or upon applied pressure or flexure.

The ability of the cross linked water soluble polymer to retain aqueous solution and its stability over extremes of ambient temperature, allow the iontophoretic drug delivery device 10 to be prepackaged and stored as a ready to use device, eliminating the need for loading a drug solution after opening and assembly.

In addition, the various reservoirs 28, 32 formed from the cross linked water soluble polymer sheet 40 are easily and stabably coupled with the electrically conductive electrodes 14, 26 to form a highly electrically conductive electrode assembly 12. Also, because of the handleability of the cross linked water soluble polymer, the medicament can either be added to the viscous water soluble polymer solution or subsequently added after cross linking depending upon the application and/or the medicament to be administered.

As previously discussed, the two portions of the device 20, 22 are placed over the applied area, i.e., the portion of the skin where the medicament is to be delivered such as the arm as illustrated in FIG. 1 with other electrode 32, i.e., the return electrode, placed on the skin 60 at an appropriate location relative to the first or working electrode 14.

Further, the cross linked water soluble polymer 40 in the preferred embodiment of the present invention is self-adhering to the skin of the patient and therefore provides intimate contact for ionic transport. Accordingly, the cross linked water soluble polymer sheet 40 contained in the drug reservoir 28 and used for the electrolyte reservoir 32 may also act as an adhesive, eliminating the need in prior devices for an adhesive layer or the like.

The following formulations for the cross linked water soluble polymer sheet 40 were used in connection with the device of the present invention for the reservoirs in the iontophoretic delivery of a topical anesthetic and a vasoconstrictor, with the device 10 including one active electrode 24 having a surface area between 2–10 $cm^2$ and one to three return electrodes 26 having a total surface area between 1–5 cm². The electrode reservoir 28 was comprised of the following active and inert components to a thickness of between 10–50 mils by making a viscous stock solution containing the medicaments and the excipients that was 3 times more concentrated than the intended final formulation. The stock solution was then added to pre-existing sheets as one part solution to two parts sheet (by weight) and allowed to diffuse and equilibrate in the sheets.

EXAMPLE 1

| Active Components | Inert Components | Concentration (%, w/w) | Mass per 2.5 cmsq (mg) |
|---|---|---|---|
| Lidocaine hydrochloride, U.S.P. | | 10.00 | 45.000 |
| Epinephrine Bitartrate | | 0.10 | 0.450 |
| | Glycerin, U.S.P. | 10.00 | 45.000 |
| | Cross linked polyvinyl pyrrolidone (PVP), U.S.P. | 16.67 | 75.020 |
| | Sodium metabisulphite, U.S.P. | 0.05 | 0.230 |
| | EDTA disodium, U.S.P. | 0.01 | 0.045 |
| | Citric acid, U.S.P. | 0.02 | 0.090 |
| | Water | 63.15 | 450 |
| | Total | 100.00 | 450.000 |

In the preferred embodiment, the Lidocaine is an anesthetic, the Epinephrine Bitartrate ("Epinephrine") is a vasoconstrictor, and the composition of PVP is 10% to 20%, preferably 15%, known as K-90F from BASF Corp. However, it should be appreciated that the concentration of the PVP may vary from approximately 10% to 60% w/w. In addition, it should be appreciated that L-Adrenaline can be substituted for the Epinephrine.

After cross-linking the gel material of Example 1 having 25% PVP, 75% water and 1% preservative PHENONIP manufactured NIPA Corporation by exposure to 2 Mrad (20 kGy) and loaded with drug and excipients, it was found that this gel material when applied to an electrode comprised of silver/silver chloride ink printed onto a polyester substrate, such that the surface resistance is less than 3 ohm per square, and the dried coating is porous yielded an average adhesive strength greater than 40 grams/inch which was on average greater than the cohesive strength (peel strength) of the gel material as evident by gel material tearing apart upon peeling, which remained on the electrode surface. Despite this relatively low cohesive strength, it was still sufficiently greater than the adhesive strength to the skin as evident by little, if any, gel material remaining on the skin upon removal of the reservoir.

In another, after cross-linking the gel material of Example 1 having 25% PVP, 75% water and 1% preservative PHENONIP manufactured NIPA Corporation by exposure to 1.5 Mrad (15 kGy) and loaded with drug and excipients, it was found that this gel material when applied to an electrode comprised of silver/silver chloride ink printed onto a polyester substrate, such that the surface resistance is less than 3 ohm per square, and the dried coating is porous yielded an average adhesive strength greater than 60 grams/inch which was on average greater than the cohesive strength (peel strength) of the gel material as evident by gel material tearing apart upon peeling, which remained on the electrode surface. Despite this relatively low cohesive strength, it was still sufficiently greater than the adhesive strength to the skin as evident by little, if any, gel material remaining on the skin upon removal of the reservoir.

EXAMPLE 2

Same as Example 1, however, Polyethylene oxide (PEO) NF was substituted for the PVP with the unloaded reservoir polymer concentration being around 1% to 6%, preferably 5.0%, however, it should be appreciated that the concentration of the PEO may varying from approximately 1–10% w/w depending upon its molecular weight.

Further, material remaining on the electrode is preferred as evidencing intimate contact between the electrode and the reservoir.

EXAMPLE 3

Same as Example 1, with polyvinyl alcohol (PVA) being substituted for the PVP, and the preferred unloaded reservoir polymer concentration of the PVA varying from approximately 10–30% w/w.

EXAMPLE 4

Same as Example 1, with polyethylene glycol (PEG) being substituted for the PVP, and the preferred unloaded reservoir polymer concentration of the PEG varying from approximately 20–60% w/w.

EXAMPLE 5

Same as Example 1, with the addition of about 5–20% glycerin, preferably 10%, to the reservoir to keep the aqueous drug solution form diffusing into all other phases in contact with the reservoir which is defined herein as a "synerisis inhibitor".

Each of the above applications involved the use of devices for the delivery of Lidocaine and Epinephrine for short application times, i.e., less than 30 minutes.

Drug, medication, medicament and active compound have been used herein to mean any ionicly charged pharmaceutical agent, such as therapeutic compounds, diagnostic agents and the like.

In addition, it should be appreciated that the device and reservoir of the present invention may be packaged in a nitrogen rich environment as disclosed in co-pending application Ser. No. 08/316,741 now abandoned, the disclosure of which is hereby incorporated by reference.

Further, while the present invention has been described in connection with iontophoresis, it should be appreciated that it may be used in connection with other principles of electroactive introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field. Also, it should be appreciated that the patient may include humans as well as animals.

While the preferred embodiments of the present invention have been described so as to enable one skilled in the art to practice the device and method of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

While this invention is satisfied by embodiments in many different forms, there are shown in the drawings and herein described in detail, embodiments of the invention with the understanding that the present disclosure to be considered as exemplary of the principles of the present invention and is not intended to limit the scope of the invention to the embodiments illustrated. The scope of the invention is measured by the appended claims and the equivalents.

Referring to FIGS. 5–8, a reservoir electrode assembly 110 of the present invention for an iontophoretic drug delivery device includes an electrode 112 and a hydrophilic reservoir 114 situated in electrically conductive relation to electrode 112. Hydrophilic reservoir 114 is formed from a bibulous hydrophilic cross-linked polymeric material 116 having a first surface 118 and a second surface 120 that is adhesively adherent to electrode 112. First surface 118 of polymeric material 116 is releasably adhesively adherent when applied to an area 122 of a patient's skin. Polymeric material 116 has a cohesive strength and forms an adhesive bond 124 with a bond strength between second surface 120 of the polymeric material to electrode 112 that is greater than the cohesive strength of polymeric material 116. Additionally, an adhesive bond strength of first surface 118 of polymeric 116 material to applied area 122 of the patient is less than the cohesive strength of polymeric material 116 so that upon removal of reservoir assembly 100 of the invention from the applied area of the patient, substantially no polymeric material 116 remains on applied area 122 and hydrophilic reservoir 114 remains substantially intact and adhesively adherent to electrode 112. Adverting to FIG. 6, reservoir electrode assembly 110 preferably includes a reinforcement 126 to provide two-dimensional stability, indicated by reference characters x and y, to polymeric material 116 and allow a swelling of polymeric material 116 in a third dimension z. Reinforcement 126 may be formed from a woven material or a non-woven material. Preferably, reinforcement 126 is formed from a non-woven material with a basis weight about ten to about thirty grams per square meter. Reinforcement 126 is preferably disposed in a layer 128 substantially intermediate first surface 118 and said second surface 120 of bibulous hydrophilic polymeric material 116 so that when polymeric material 116 imbibes an aqueous solution, swelling of polymeric material 116 is substantially limited to increasing a distance "d" between first surface 118 and second surface 120. Preferably, first surface 118 and second surface 120 are substantially parallel to each other. Suitable non-woven materials are available from Reemay as a spun-bonded poly(ethyleneterephthalate) 2004 (PET) with a basis weight of about 14 grams per square meter. Other materials with other basis weights may be preferred for particular applications and are considered within the scope of this disclosure.

A preferred material for forming hydrophilic reservoir 114 is poly(vinylpyrollidone) (PVP) with a number average molecular weight greater than about 360,000 daltons. A suitable PVP is available from BASF, NJ as PVP K-90F. When this material is prepared as a concentrated aqueous solution it forms a viscous syrup which is preferably applied to both sides of the reinforcement 126, placed between two release webs to a thickness of about of about 40 mils and subjected to ionizing radiation sufficient to cross-link the PVP sufficiently to substantially be shape retaining, flexible and having a degree of tack. A preferred ionizing radiation is an electron beam having at least about a 1 MeV to deliver between about 1.5 and 2.5 megarads. Other sources of ionizing radiation such as $^{60}$Co or $^{137}$Cs may be used for particular applications. The degree of cross-link has considerable effect on the degree of tack. If there is insufficient cross-linking, resultant PVP reservoir 114 does not retain shape, may detach from reinforcement 126 and is extreme difficult to handle. If the degree of cross-linking is too great, the resultant PVP reservoir 114 has insufficient tack to adhere to electrode 112 or to patient contact area 122.

The use of the electron beam for cross-linking the PVP for reservoir 114 has a particular benefit to the present invention. Unlike gamma radiation that has a potential penetration of several feet of concrete, the electron beam penetration depth is described in the units of cm of water. This property of the electron beam can be utilized in controlling the degree of cross-link in reservoir 114. The exposure can be controlled so that there is a differential degree of tack on surface 118 than on surface 120 of reservoir 114. The differential degree of tack on the first surface and the second surface may be preselected to allow a sufficient degree of tack on surface 120 to ensure a sufficiently strong bond between electrode 112 and reservoir 114 to substantially prevent separation of the electrode and the reservoir while allowing the reservoir to be removed from the patient's skin.

The preferred degree of cross-link is determined by the degree of tack as described below. The preferred which results in a swelling ratio of greater than 3. Additionally, because the bibulous material is constrained in the "x" and "y" directions by the reinforcement 126, best seen in FIG. 6, the swelling that occurs upon imbibement of aqueous solution, preferably occurs substantially only in the "z" direction, i.e., to increase the distance "d" between first surface 118 and second surface 120.

The manufacture of hydrophilic reservoir 114 is preferably begun with a web of reinforcement 126 being coated on both sides with a viscous solution of the PVP with a concentration of between about twenty percent to about thirty percent, preferably about 24 percent, (w/w) in an aqueous solution. When prepared in this fashion, the preferred PVP solution has a viscosity similar to that of molasses and is adherent to reinforcement 126. As the coating of PVP is applied, web 126, with the coating is preferably sandwiched between two release liners. Preferably, one of the release liners 130 is formed from a stiff polymeric material, such as PET coated with polyethylene or silicone and the like. Stiff release liner 130 serves as an anvil for die cutting out sections of hydrophilic reservoir 114 in the shape desired for incorporation into the iontophoretic device electrode reservoir assembly. Once the PVP is coated onto reinforcement 126 and placed between the release liners, the entire web, i.e., reinforcement 126, the PVP coating and the release liners, is exposed to the preselected dose of ionizing radiation for cross-linking. Preferably, the thickness of the cross-linked material is between about 35 to about 45 mils. For particular applications, other thickness may be preferred. Upon cross-linking, the reinforced PVP reservoir material preferably has a cohesive strength, a tackiness sufficient to adhere releasably to a patient's skin and to form an adhesive bond 124 with conductive ink electrode 112 on a flexible substrate 140. Preferably, the adhesive bond formed between reservoir 114 and conductive ink electrode 112 is stronger that the cohesive strength of the cross-linked PVP used to form the reservoir. This strong bond between electrode 112 and reservoir 114 ensures good electrical contact and substantially prevents the reservoir from detaching from the electrode. Additionally, it is also preferred that the strength of adhesive bond 124 formed between the reservoir 114 and conductive ink electrode 112 is stronger than an adhesive bond formed between the surface of the patient's skin and reservoir 114 and that the cohesive strength of the reservoir is greater than the strength of the adhesive bond between the patient's skin and the reservoir. This substantially ensures that when reservoir 114 is removed from the patient's skin, the reservoir is substantially removed from the patient's skin, leaving substantially no residue.

In addition to the PVP in aqueous solution, preferably, the coating solution may also include preservative materials to inhibit microbial growth such as para-benzoic acid (paraben) and the like. A suitable preservative includes a series of mixed parabens including, methyl paraben, ethyl paraben, n-propyl paraben, iso-propyl paraben, n-butyl paraben and 2-phenoxyethanol and is sold under the tradename "Phenonip" by Nipa Laboratories, Wilm. Del. In the present invention, the material has been shown effective at substantially preventing microbial growth at a concentration of about one-percent in the 24% aqueous PVP solution. A further benefit of the radiation cross-linking of the PVP with preservative is that the radiation dose used for cross-linking is sufficient to substantially eliminate most microorganisms and the presence of the preservative then substantially inhibits and further growth after loading and during shelf storage.

A preferred technique for measuring tack is called described in an ASTM method No. D3121-94 entitled: "TACK ROLLING BALL METHOD" (TRBM). This standardized test method utilizes a standard inclined trough that delivers a standard ball bearing onto the surface of the material being tested. The ball is released from a standard height in the trough onto the surface of the test material and a measurement is made of the distance in mm that the ball rolls on the surface being tested. The greater the tack exhibited by the test material, the shorter the distance the ball rolls. For the preferred cross-linked PVP used in reservoir 114, the TRBM values are preferably between about 15 mm to about 40 mm. If the tack is substantially greater than the preferred value, reservoir 114 may lack cohesive strength and not be shape retaining. If the tack is substantially less than the preferred value, there is insufficient adherence to the skin and to the electrode. Other methods of measuring adhesive ability are also useful for characterizing the preferred cross-linked PVP. These methods include the probe tack and peel from steel. These tests are useful to characterize the cross-linked hydrophilic polymeric material used to form reservoir 114. An empirical description of the preferred material is that, when cut into discs of the a size about 5 square centimeters, the discs are sufficiently adherent when loaded with the aqueous medicament to be lifted after a gentle pressure with an index finger on the surface of the disc.

When cross-linked PVP as described above is used in an iontophoretic device of the invention, the PVP concentration is preferably about twenty-four percent w/w and after imbibement of an aqueous solution of the desired medicament to be delivered, the PVP concentration is about fifteen percent. Other reservoirs used in iontophoretic devices have significantly higher concentrations of materials required as carriers. The reservoir of the invention in having only about fifteen percent PVP provides the an unexpected benefit to the art by allowing the reservoir to be physically smaller and to increase the efficiency of the drug delivery by making the drug more available for delivery and to provide sufficient tack to both patient skin and electrode to ensure substantially uniform electrical contact.

An example of a drug delivery system using the reservoir assembly of the invention is prepared as follows. A solution of poly(vinylpyrolidone), (PVPK90-F BASF) at a concentration of 24% w/w containing 1% w/w mixed parabens (Phenonip, Nipa Laboratories) in 0.06% sodium chloride was prepared. After thorough mixing the resultant viscous solution was coated onto both sides, best seen in FIG. 7, of a reinforcement (Reemay 2004, spun bonded polyester to a thickness of about 40 thousandths of an inch (40 mils). The coated reinforcement was applied to a release liner 132 formed form low density polyethylene (LDPE) film on one side and stiffer laminate 130 of 2 mil polyester and 2 mil LDPE disposed so that the LDPE laminate was on the other side of the viscous solution. The material was then exposed to electron beam irradiation with the LDPE film was closest to the source of the electron beam energy. A dosage of about 2 megarad was administered to the material causing the PVP to cross-link. LDPE film 132 was then removed from one side of the PVP and the material was cut into the desired, best seen in FIGS. 6 and 8, five square centimeter shapes for the active electrode. The material with laminate release liner 132 remaining on the other side was bonded on exposed side 120 onto a flexible substrate coated with conductive ink electrode 112 containing silver and silver chloride in a suitable vehicle covering between about 60% to about 90% of the surface are of substrate 140 in the region where reservoir 114 is positioned, preferably about 90% of its surface with a loading of one and one half to about five grams of ink per square centimeter of surface area. By keeping the coverage of the ink electrode below about 90%, direct contact between the patient's skin and the ink electrode is substantially precluded. After cross-linked material 114 is bonded to flexible ink electrode 112, reservoir 114 is ready to be loaded with the aqueous drug solution.

Flexible ink electrode 112 containing silver and silver chloride is applied to the flexible substrate to connect the power source to the reservoir 114. The ink preferably has a resistivity of less than about 120 ohms per square. A suitable ink is available from E.I.du Pont de neumours, Wilm. Del. The terminology of "ohms per square" is developed from the thin film electrode art. A term "ohm-cm" is used to define the specific resistance or resistivity of a material and is labeled by the Greek letter P (RHO). Since the metric system is the standard measuring used in laboratories. P is defined as the number for ohms resistance between parallel faces of a cubic centimeter of a material. Every material has a specific conductivity, so P is different for each material. This term is also known as ohms per centimeter cubed. In the case where the material is in the form of a thin (i.e., about 0.00025 cm to about 0.025 cm ) the term is defined as ohms per square. This is defined as the resistance of a square surface area of film and is independent of the size of the square. In the first instance R=PL/A, in the case of a film A=Wt, where t is the thickness of the film so that now R=PL/Wt, since L=W for any size square, this leads to R=P?t. As P is a constant for any given material, it is apparent that R varies inversely as the film thickness. As a consequence, when a resistance is specified in ohms per square and the resistivity of the conductive ink or film is known, the effective film thickness is thus specified. In the instant example, a preferred thickness is achieved with at loading of between about one and one-half to about five grams of conductive ink per square centimeter of surface for electrode 112 which provides a resistivity of less than bout 120 ohms.

In the present example, an aqueous loading solution of 30% lidocaine HCl, 3% epinephrine, 30% glycerin, 0.05% sodium metabisulfite, 0.03% ethylene diamine tetraacetic acid, and 0.06% citric acid are used for the loading solution. The medicaments for delivery are lidocaine HCl and epinephrine, the glycerin serves as a humectant, the other minor components serve to enhance drug stability by chelating metal ions and serving as antioxidants. In order to load this solution onto the reservoir with electrode 112, laminate release liner 132 is removed from side 118 of reservoir 114 and a three-hundred microliter aliquot of this loading solution is applied to exposed surface 118, which is then covered with a final cover that remains in place until the reservoir is applied to a patient to protect the reservoir. Other aqueous formulations of other medicaments and other concentrations may be envisioned for the electrode assembly of the invention and are to be considered within the scope of the invention. The electrode assembly 110 of the invention when loaded with the aqueous medicament solution described above has demonstrated sufficient shelf stability when stored in a package formed from materials substantially resistant to the passage of moisture and oxygen at accelerated, ambient and cycled temperatures for two years.

A counter electrode assembly for the iontophoretic device of the invention is formed by cutting a second shape from the cross-linked PVP with a surface area of about 2.75 square centimeter area. A counter electrode reservoir is assembled in the same fashion as the active electrode described above. This counter electrode reservoir is preferably loaded with an aqueous solution containing about 30% glycerin, 1% mixed parabens, 0.06% sodium chloride. The aqueous carrier for both of the solutions preferably meets the standard for purified water in the USP XXXIII.

It has been shown that if the loading solutions are not loaded substantially uniformly across surface 118 of reservoir 114, that localized thickness variations of the reservoir may develop in the cross-linked PVP with adverse effects on attachment to electrode 112 and subsequent attachment to the patient. Additionally, the localized concentration differentials of chloride ion may facilitate deterioration of the silver/silver chloride electrode. Therefore, it is preferred that the loading solutions be substantially uniformly loaded across surface 118 of the electrode reservoir. For the active electrode containing the lidocaine and epinephrine, a loading level of about three hundred microliters is preferred for a five square centimeter, forty-thousandths thick reservoir with a uncharged volume of about 0.5 cc resulting in a charged volume of about 0.8 cc. For the counter or return electrode with an area of about two and three-quarters square centimeter surface area, the preferred loading is about two hundred microliters of the aqueous solution.

When the cross-linked PVP material is loaded with the aqueous charging solutions, the final PVP concentration of in the electrode is reduced from about twenty-four percent to about fifteen percent. The cross-linked PVP swells to about one hundred fifty percent of its uncharged volume, and because of the reinforcement, the swelling occurs primarily in the "z" direction or increases the thickness of the reservoir 114 about sixty percent.

The reservoir electrode of the invention is an improvement to the art of iontophoretic electrode reservoirs. The reservoir is efficient in its utilization of available drug. Medicaments known to be labile, such as epinephrine, have satisfactory shelf stability when incorporated into the reservoir. Since the reservoir of the invention is flexible and adhesive, the reservoir electrode makes good uniform contact with the patient's skin, minimizing any tendency for the current to concentrate at a particular point causing irritation or burns to the patient's skin. The reservoir electrode is easily prepared and its properties such as adhesion, size and medicament loading are easily adjustable during manufacture.

What is claimed is:

1. An iontophoretic drug delivery device for delivering at least one medicament to an applied area of a patient, such as the skin, mucous membrane and the like, comprising:
   electrode assembly means, including an electrode, for driving a medication into the applied area of the patient to be absorbed by the body of the patient; and
   a covalently cross linked hydrophilic reservoir having a first surface and a second surface; wherein said second surface is situated in electrically conductive relation to the electrode assembly means, with said reservoir including an aqueous swollen cross linked water soluble polymer material having a degree of crosslinking varying from said first surface to said second surface, wherein said crosslinking results in tacky first and second surfaces that differ from one another in adhesive strength.

2. A reservoir electrode assembly for an iontophoretic drug delivery device comprising:
   an electrode; and
   a hydrophilic reservoir situated in electrically conductive relation to said electrode, said reservoir being formed from a bibulous hydrophilic cross-linked polymeric material having a first surface and a second surface being adhesively adherent to said electrode, said polymeric material having a degree of crosslinking varying from said first surface to said second surface, wherein said crosslinking results in tacky first and second surfaces that differ from one another in adhesive strength.

3. The reservoir electrode assembly of claim 2 wherein said hydrophilic reservoir further comprises a reinforcement to provide two-dimensional stability to said polymeric material and allow a swelling of said polymeric material in a third dimension.

4. The reservoir electrode assembly of claim 3 wherein said reinforcement is selected from the group consisting of a woven material and a non-woven material.

5. The reservoir electrode assembly of claim 4 wherein said reinforcement is formed from a non-woven material with a basis weight about ten to about thirty grams per square meter disposed substantially intermediate said first surface and said second surface of said bibulous hydrophilic polymeric material so that when said polymeric material imbibes an aqueous solution, said swelling of said polymeric material is substantially limited to increasing a distance between said first surface and said second surface and wherein said first surface and said second surface are substantially parallel to each other.

6. The reservoir electrode assembly of claim 5 wherein said bibulous hydrophilic polymeric material is poly (vinylpyrollidone) additionally being cross-linked to a preselected sufficient degree to be substantially shape retaining.

7. The reservoir electrode assembly of claim 6 wherein said poly(vinylpyrollidone) has a number average molecular weight above about 360,000 prior to said cross-linking.

8. The reservoir electrode assembly of claim 6 wherein said poly(vinylpyrollidone) is cross-linked by the application of a preselected quantity of ionizing radiation.

9. The reservoir electrode assembly of claim 8 wherein said poly(vinylpyrollidone) is swollen by a substantially uniform application to said first surface of an aqueous solution of at least one material selected from the group consisting of a medicament to be delivered to the patient, another medicament to be delivered to the patient, an electrolyte, another electrolyte, a preservative, a chelating agent, an antioxidant, a humectant and combinations thereof.

10. The electrode assembly of claim 2 wherein said cross-linked bibulous hydrophilic polymeric material has a swell ratio of greater than three when said bibulous hydrophilic polymeric material is charged with sufficient aqueous material to provide the preselected medicament delivery.

11. The reservoir electrode assembly of claim 2 wherein said electrode is formed from an application of a coating of an electrically conductive ink to a surface of a flexible substrate on said surface disposed against said second surface of said polymeric material.

12. The reservoir electrode assembly of claim 11 wherein said coating of said electrically conductive ink covers more than one half of said surface of said substrate disposed against said polymeric material.

13. The reservoir electrode assembly of claim 12 wherein said coating of said electrically conductive ink covers about ninety percent of said surface of said substrate disposed against said polymeric material, said ink coating being capable of being adhesively bonded to said second surface of said polymeric material.

14. The reservoir electrode assembly of claim 13 wherein said electrically conductive ink comprises silver and silver chloride.

15. The reservoir electrode assembly of claim 13 wherein said electrically conductive ink has a coat weight between about 1.5 and 5 grams per square cm.

16. The reservoir electrode assembly of claim 15 wherein said electrically coated ink has a resistivity of less than about 120 ohms per square.

17. The electrode assembly of claim 2 wherein a Tack Rolling Ball Measurement (TRBM) of the adhesive tack of the bibulous hydrophilic polymeric material is between about 5 mm to about 40 mm after cross-linking and prior to charging said reservoir with an aqueous medicament solution.

18. The electrode assembly of claim 17 wherein said TRBM of one side of said bibulous hydrophilic polymeric material is greater than about 15 mm and another side of said hydrophilic polymeric material is less than about 30 mm and wherein the TRBM of said sides are not the same.

19. A reservoir electrode assembly for an iontophoretic drug delivery device comprising:

an electrode formed from an application of a coating of an electrically conductive ink to a surface of a flexible substrate; and a hydrophilic reservoir situated in electrically conductive relation to said electrode, said reservoir being formed from a bibulous hydrophilic cross-linked polymeric material having a first surface and a second surface being adhesively adherent to said electrode, said polymeric material having a degree of crosslinking varying from said first surface to said second surface and having a reinforcement therewithin to provide two-dimensional stability to said polymeric material and allow a swelling of said polymeric material in a third dimension, wherein said polymeric material has a degree of crosslinking varying from said first surface to said second surface, wherein said crosslinking results in tacky first and second surfaces that differ from one another in adhesive strength.

20. The reservoir electrode assembly of claim 19 wherein said reinforcement is formed from a non-woven material with a basis weight about ten to about thirty grams per square meter disposed substantially intermediate said first surface and said second surface of said bibulous hydrophilic polymeric material so that when said polymeric material imbibes an aqueous solution, said swelling of said polymeric material is substantially limited to increasing a distance between said first surface and said second surface and wherein said first surface and said second surface are substantially parallel to each other.

* * * * *

UNITED STATES PATENT AND TRADEMARK OFFICE
CERTIFICATE OF CORRECTION

PATENT NO.     : 6,377,847 B1
DATED          : April 23, 2002
INVENTOR(S)    : Keusch et al.

It is certified that error appears in the above-identified patent and that said Letters Patent is hereby corrected as shown below:

<u>Title page,</u>
Item [57], ABSTRACT, insert -- which -- after "strength".

<u>Column 2,</u>
Line 2, add commas after "as" and "example"

<u>Column 3,</u>
Line 62, delete "though" and substitute therefore -- through --.

<u>Column 5,</u>
Lines 6 & 7, after "includes the", add -- step --.

<u>Column 8,</u>
Line 21, delete "he" and substitute therefore -- the --.

<u>Column 10,</u>
Line 10, delete "varying" and substitute therefore -- vary --.

<u>Column 11,</u>
Line 26, delete "100" and substitute therefore -- 110 --.

<u>Column 12,</u>
Line 3, delete "extreme" and substitute therefore -- extremely --.

<u>Column 13,</u>
Lines 24 & 25, delete "called".
Line 46, delete "the" after "of".
Line 59, delete "the" after "provides".

<u>Column 14,</u>
Line 16, after the word "desired" insert -- shape --.
Line 52, delete "R=P?t" and substitute therefore -- R=P/t --.

UNITED STATES PATENT AND TRADEMARK OFFICE
CERTIFICATE OF CORRECTION

PATENT NO.   : 6,377,847 B1
DATED        : April 23, 2002
INVENTOR(S)  : Keusch et al.

It is certified that error appears in the above-identified patent and that said Letters Patent is hereby corrected as shown below:

Column 15,
Line 47, delete "of" after "concentration".

Signed and Sealed this

Twenty-eighth Day of October, 2003

JAMES E. ROGAN
*Director of the United States Patent and Trademark Office*